(12) United States Patent
Andresen et al.

(10) Patent No.: US 10,056,688 B2
(45) Date of Patent: Aug. 21, 2018

(54) PATCH ANTENNA ASSEMBLY

(71) Applicant: Micron Devices LLC, Miami Beach, FL (US)

(72) Inventors: Chad David Andresen, Miami Beach, FL (US); Richard LeBaron, Miami Beach, FL (US); Laura Tyler Perryman, Miami Beach, FL (US)

(73) Assignee: Micron Devices LLC, Pompano Beach, FL (US)

( * ) Notice: Subject to any disclaimer, the term of this patent is extended or adjusted under 35 U.S.C. 154(b) by 394 days.

(21) Appl. No.: 14/986,379

(22) Filed: Dec. 31, 2015

(65) Prior Publication Data

US 2016/0190698 A1   Jun. 30, 2016

Related U.S. Application Data

(60) Provisional application No. 62/098,900, filed on Dec. 31, 2014.

(51) Int. Cl.
*A61N 1/372* (2006.01)
*H01Q 9/04* (2006.01)

(52) U.S. Cl.
CPC ....... *H01Q 9/0442* (2013.01); *A61N 1/37223* (2013.01); *A61N 1/37229* (2013.01)

(58) Field of Classification Search
CPC .............. H01Q 9/0442; A61N 1/37223; A61N 1/37229

(Continued)

(56) References Cited

U.S. PATENT DOCUMENTS 4,972,196 A * 11/1990 Mayes ................. H01Q 9/0457
343/700 MS
5,767,808 A   6/1998 Robbins et al.
(Continued)

FOREIGN PATENT DOCUMENTS

CA   2218269      4/1999
CA   2218269 A1 * 4/1999  ............... H01Q 1/38
(Continued)

OTHER PUBLICATIONS

International Search Report in International Application No. PCT/US2015/068343, dated Mar. 18, 2016, 3 pages.
(Continued)

*Primary Examiner* — Michael Carey
(74) *Attorney, Agent, or Firm* — Fish & Richardson P.C.

(57) ABSTRACT

A patch antenna assembly that includes a signal metal layer configured to emit linearly polarized electromagnetic energy to a receiving antenna implanted up to 12 cm underneath a subject's skin; a signal metal layer substrate on which the signal metal layer substrate is positioned; a ground plane located next to the signal metal layer substrate and further away from the subject's skin; a microstrip and capacitance adjustment pad metal layer substrate located next to the ground plane; and a microstrip and capacitance adjustment pad metal layer next to the microstrip and capacitance adjustment pad metal layer substrate, the microstrip and capacitance adjustment pad metal layer comprising: a capacitance adjustment pad configured to adjust a resonant frequency of the patch antenna assembly; and a microstrip attached to the capacitance adjustment pad and configured to induce the emitted electromagnetic energy to be linearly polarized along a longitudinal direction of the microstrip.

20 Claims, 13 Drawing Sheets

(58) Field of Classification Search
USPC .................................. 607/60, 2, 65, 59, 116
See application file for complete search history.

(56) References Cited

U.S. PATENT DOCUMENTS

| | | | |
|---|---|---|---|
| 5,828,340 A | 10/1998 | Johnson | |
| 5,861,019 A * | 1/1999 | Sun | H01Q 1/273 607/36 |
| 2008/0258978 A1 | 10/2008 | Stuart | |
| 2010/0109966 A1 | 5/2010 | Mateychuk et al. | |
| 2010/0321191 A1 | 12/2010 | Gong et al. | |
| 2011/0288615 A1 | 11/2011 | Armstrong et al. | |
| 2012/0276856 A1 | 11/2012 | Joshi et al. | |
| 2014/0031889 A1 | 1/2014 | Mashiach | |
| 2014/0180365 A1 * | 6/2014 | Perryman | H01Q 1/40 607/60 |
| 2014/0336727 A1 * | 11/2014 | Perryman | A61N 1/37229 607/59 |

FOREIGN PATENT DOCUMENTS

| | | |
|---|---|---|
| GB | 2427759 | 1/2007 |
| WO | WO2008/094775 A2 | 8/2008 |
| WO | WO2008/094775 A3 | 8/2008 |
| WO | WO2010/051249 | 5/2010 |
| WO | WO2013/040549 | 3/2013 |
| WO | WO2013/147470 | 10/2013 |
| WO | WO2013/147799 | 10/2013 |

OTHER PUBLICATIONS

Extended European Search Report in European Application No. 15876379.7. dated Jun. 28, 2018, 6 pages.

* cited by examiner

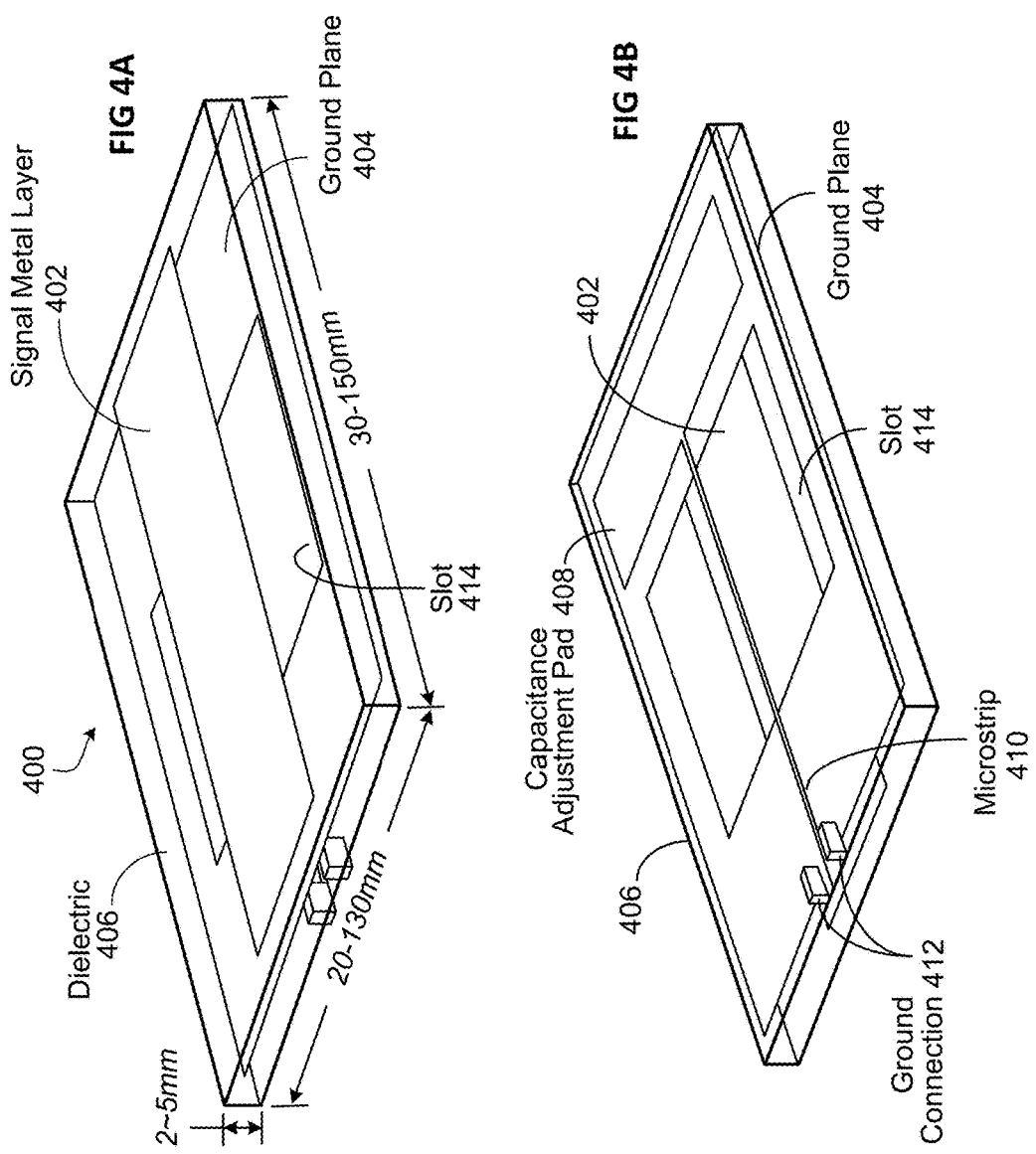

| Signal Metal Layer | 402 |
|---|---|
| Signal Metal Layer Substrate | 602 |
| Ground Plane Metal Layer | 604 |
| Microstrip and capacitance adjustment Pad Metal Layer Substrate | 606 |
| Microstrip and Capacitance Adjustment Pad Metal Layer | 608 |

FIG. 6

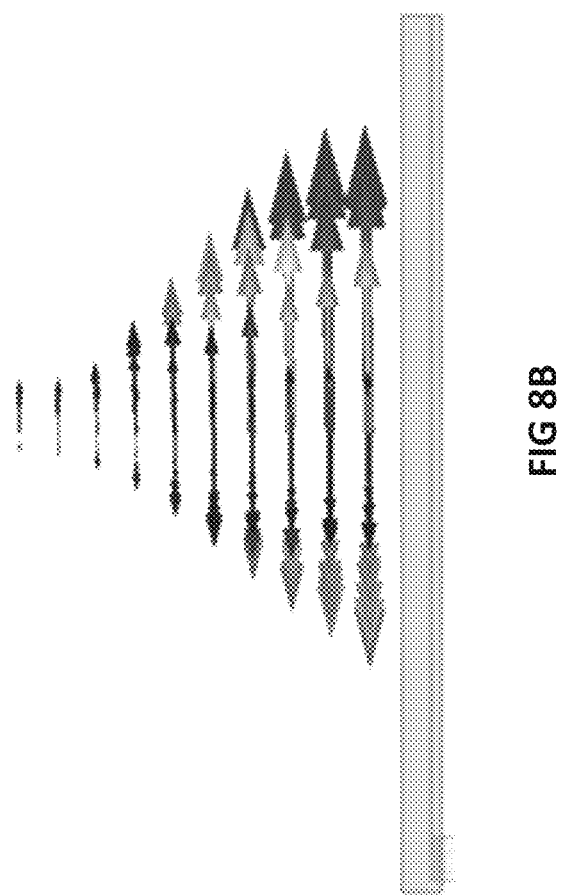

PATCH ANTENNA ASSEMBLY

CROSS REFERENCE TO RELATED APPLICATIONS

This application claims benefit of U.S. provisional Patent Application 62/098,900, filed Dec. 31, 2014, which is hereby incorporated by reference in its entirely.

TECHNICAL FIELD

This application relates generally to an antenna assembly to couple energy to an implanted medical device.

BACKGROUND

Modulation of excitable tissue in the body by electrical stimulation has become an important type of therapy for patients with chronic disabling conditions, including pain, movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide a patch antenna assembly that includes a signal metal layer configured to emit linearly polarized electromagnetic energy to a receiving antenna implanted up to 12 cm underneath a subject's skin, and oriented to face the subject's skin when the patch antenna assembly is worn by the subject; a signal metal layer substrate on which the signal metal layer substrate is positioned; a ground plane located next to the signal metal layer substrate and further away from the subject's skin than the signal metal layer when the patch antenna assembly is worn; a microstrip and capacitance adjustment pad metal layer substrate located next to the ground plane and away from the signal metal layer; and a microstrip and capacitance adjustment pad metal layer next to the microstrip and capacitance adjustment pad metal layer substrate and away from the signal metal layer, the microstrip and capacitance adjustment pad metal layer including: a capacitance adjustment pad configured to adjust a resonant frequency of the patch antenna assembly; and a microstrip attached to the capacitance adjustment pad and configured to induce the emitted electromagnetic energy to be linearly polarized along a longitudinal direction of the microstrip.

Implementations may include one or more of the following features.

The patch antenna assembly may be configured to operate with a reflection ratio of at least 10 dB, the reflection ratio corresponding to a ratio of a transmission power used by the patch antenna assembly to emit the linearly polarize electromagnetic energy and a reflection power seen by the patch antenna assembly resulting from electromagnetic emission using the transmission power. The reflection ratio of at least 10 dB may be maintained regardless of a separation between the signal metal layer and the subject's skin. The patch antenna assembly may be configured such that the reflection ratio of at least 10 dB is maintained with an air gap and without gel coupling between the signal metal layer and the subject's skin. The capacitance adjustment pad may be configured to adjust the resonant frequency of the patch antenna assembly to be matched at the resonant frequency of the RF signal generator. The patch antenna assembly may be configured to operate with a quality factor (Q) no more than 9.

The patch antenna assembly may have a size that is no more than 40% of a wavelength of the emitted electromagnetic energy. The patch antenna assembly may have a length between 30 and 150 mm, a width between 20 and 130 mm, and a thickness between 2 and 5 mm. The signal metal layer substrate may be about 2 mm thick, the microstrip and capacitance adjustment pad metal layer substrate may be about 0.6 mm thick, and the capacitance adjustment pad metal layer may be about 70 μm thick.

The patch antenna assembly may be configured to operate at a particular frequency between 800 MHz and 5.7 GHz. The ground plane may include a slot sized and shaped to determine a resonant frequency of the patch antenna assembly. The capacitance adjustment pad may be configured to adjust the resonant frequency of the patch antenna assembly by an order of KHz. The patch antenna assembly may include a dielectric layer between the signal metal layer and the ground plane, the dielectric layer constructed to improve a coupling of the emitted linearly polarized electromagnetic energy from the microstrip to the signal metal layer relative to when the dielectric layer is absent. The microstrip may be sized and shaped for a 50Ω line impedance in the presence of the dielectric layer.

In another aspect, some implementations provide a system that includes a Radio Frequency (RF) signal generator configured to be worn by a subject and programmed to generate an input signal containing electrical energy and stimulation pulse parameters, and a patch antenna assembly coupled to the signal generator and configured to receive the input signal from the signal generator and then transmit the input signal to a receiving dipole antenna of a passive stimulator device implanted up to 12 cm underneath the subject's skin such that the patch antenna assembly operates with a reflection ratio of at least 10 dB, the reflection ratio corresponding to a ratio of a transmission power used by the patch antenna assembly to transmit the input signal and a reflection power seen by the patch antenna assembly resulting from electromagnetic emission using the transmission power, the patch antenna assembly including: a signal metal layer configured to transmit the input signal using linearly polarized electromagnetic energy to the receiving dipole antenna, and oriented to face the subject's skin when the patch antenna assembly is worn by the subject; a signal metal layer substrate on which the signal metal layer substrate is positioned; a ground plane located next to the signal metal layer substrate and further away from the subject's skin than the signal metal layer when the patch antenna assembly is worn; a microstrip and capacitance adjustment pad metal layer substrate located next to the ground plane and away from the signal metal layer; and a microstrip and capacitance adjustment pad metal layer next to the microstrip and capacitance adjustment pad metal layer substrate and away from the signal metal layer, the microstrip and capacitance adjustment pad metal layer including: a capacitance adjustment pad configured to adjust a resonant frequency of the patch antenna assembly; and a microstrip attached to the capacitance adjustment pad and configured to induce the emitted electromagnetic energy to be linearly polarized along a longitudinal direction of the microstrip; and a passive neural stimulator device configured to be implanted underneath the subject's skin, the passive neural stimulator device including: a receiving dipole antenna configured to receive the input signal emitted from the antenna assembly; and circuitry coupled to the receiving dipole antenna, the circuitry being configured to: extract electric energy contained in the input signal; and use the extracted electrical energy to create stimulation pulses suitable for stimulating neural tissue, the stimulation pulses being created according to the stimulation pulse parameters.

Implementations may include one or more of the following features.

The capacitance adjustment pad may be configured to adjust the resonant frequency of the patch antenna assembly to match the resonant frequency of the RF signal generator. The capacitance adjustment pad may be configured to adjust the patch antenna assembly by an order of KHz. The patch antenna assembly may be configured to operate with a quality factor (Q) no more than 9. The patch antenna assembly may include a dielectric layer that separates the signal metal layer from the ground plane, the dielectric layer constructed to improve a coupling of the emitted linearly polarized electromagnetic energy from the microstrip to the signal metal layer relative to when the dielectric layer is absent. The microstrip may be sized and shaped for a 50Ω line impedance in the presence of the dielectric layer.

The details of one or more implementations are set forth in the accompanying drawings and the description below. Other features, objects, and advantages will be apparent from the description and drawings, and from the claims.

BRIEF DESCRIPTION OF THE DRAWINGS

FIGS. 4A-4B show an example of a transmitting antenna configured as a patch antenna assembly.

FIG. 6 shows an example of a layer configuration for a patch antenna assembly.

FIG. 8A-8B show examples of polarization patterns of electromagnetic radiation from a patch antenna assembly.

Like reference symbols in the various drawings indicate like elements.

DETAILED DESCRIPTION

Figure 1:
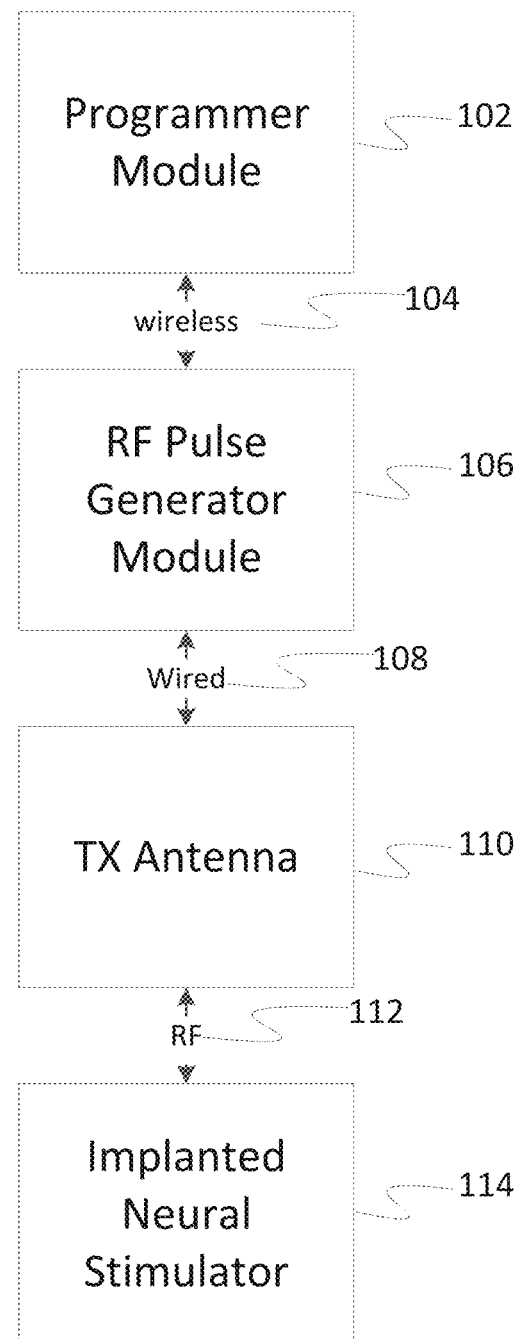
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power a passive implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for frequency waveform and electrical energy rectification. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This allows such devices to produce electrical currents capable of stimulating nerve bundles without a physical connection to an implantable pulse generator (IPG) or use of an inductive coil.

Some implementations may include a patch antenna assembly and a signal generator coupled to the patch antenna assembly. The signal generator may provide the input signal that contains electrical energy and stimulation pulse parameters. The patch antenna assembly may transmit the input signal via radiative coupling to a receiving dipole antenna of a passive wireless stimulator device implanted inside a subject such that the stimulator device is wireless powered solely using the input signal. The patch antenna may be sized and shaped with a small profile and footprint, rendering it suitable for to be worn by a subject such that displacement can be reduced when the patch antenna is worn. The patch antenna can operate without direct contact to the subject's skin. In some instances, the patch antenna can operate without a coupling gel. Particularly, the patch antenna can operate with an air gap between a top surface of the patch antenna assembly and the subject's skin. The patch antenna assembly may include a signal metal layer that faces the subject's skin when the patch antenna assembly is worn. The patch antenna may include a ground plane located below the signal metal layer and further away from the skin. The ground plane may include a slot sized and shaped to determine a resonant frequency of the patch antenna assembly. A dielectric layer may be located between the signal metal layer and the ground plane to improve coupling. The patch antenna assembly may further include a microstrip and capacitance adjustment pad metal layer. The microstrip and capacitance adjustment pad metal layer includes: a capacitance adjustment pad sized to fine tune the patch antenna assembly such that the patch antenna assembly becomes better tuned to the receiving dipole antenna within a resonant frequency of receiving dipole antenna; and a microstrip attached to the capacitance adjustment pad and configured to induce the emitted electromagnetic waves to be linearly polarized along a longitudinal direction of the microstrip.

Further descriptions of exemplary wireless systems for providing neural stimulation to a patient can be found in commonly-assigned, co-pending published PCT applications PCT/US2012/23029 filed Jan. 28, 2011, PCT/US2012/32200 filed Apr. 11, 2011, PCT/US2012/48903, filed Jan. 28, 2011, PCT/US2012/50633, filed Aug. 12, 2011 and PCT/US2012/55746, filed Sep. 15, 2011, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmit (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrode pulses, and adjust feedback sensitivity of the RF pulse generator module 106, among other functions.

The RF pulse generator module 106 may include communication electronics that support the wireless connection 104, the stimulation circuitry, and the battery to power the generator electronics. In some implementations, the RF pulse generator module 106 includes the TX antenna embedded into its packaging form factor while, in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neuronal tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 (or cylindrical wireless implantable stimulator device 1400 shown in FIGS. 14A and 14B, helical wireless implantable stimulator device 1900 shown in FIGS. 19A to 19C) can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation current for maintaining effective neuronal activation, or, in some cases, the patient can manually adjust the output signals in an open loop control method.

Figure 2:
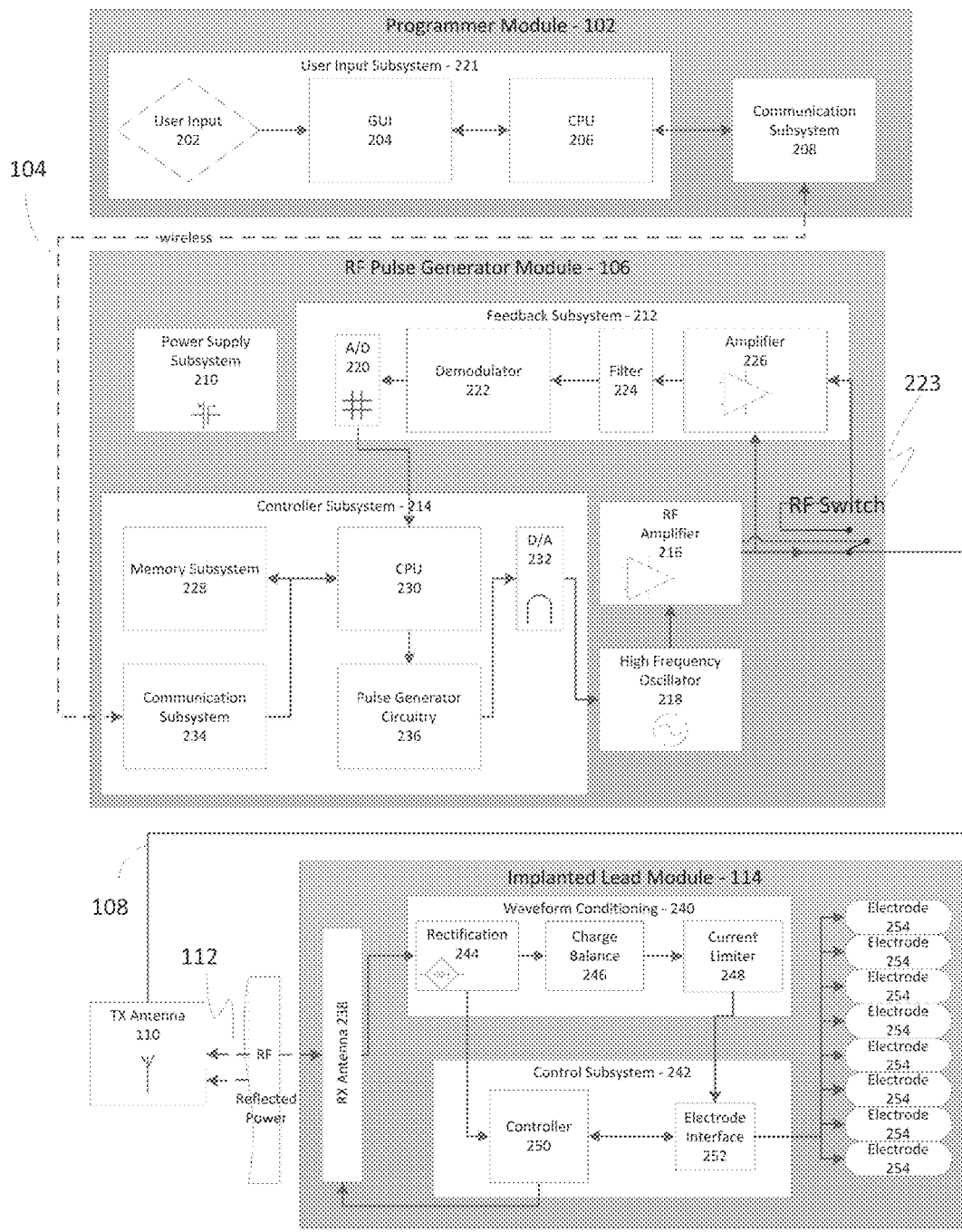
FIG. 2 depicts a detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
|---|---|
| Pulse Amplitude: | 0 to 25 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure.

Because medical conditions or the body itself can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuro-anatomy, protocols for neural modulation, and safety limits of electrical stimulation.

The controller subsystem 214 may store received parameter settings in the local memory subsystem 228, until the parameter settings are modified by new input data received from the programming module 102. The CPU 206 may use the parameters stored in the local memory to control the pulse generator circuitry 236 to generate a stimulus waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a telemetry signal may also be transmitted to the wireless stimulator device 114 to send instructions about the various operations of the wireless stimulator device 114. The telemetry signal may be sent by the modulation of the carrier signal (through the skin if external, or through other body tissues if the pulse generator module 106 is implanted subcutaneously). The telemetry signal is used to modulate the carrier signal (a high frequency signal) that is coupled onto the implanted antenna(s) 238 and does not interfere with the input received on the same stimulator device to power the device. In one embodiment the telemetry signal and powering signal are combined into one signal, where the RF telemetry signal is used to modulate the RF powering signal, and thus the wireless stimulation device is powered directly by the received telemetry signal; separate subsystems in the wireless stimulation device harness the power contained in the signal and interpret the data content of the signal.

The RF switch 223 may be a multipurpose device such as a dual directional coupler, which passes the relatively high amplitude, extremely short duration RF pulse to the TX antenna 110 with minimal insertion loss while simultaneously providing two low-level outputs to feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110.

During the on-cycle time (when an RF signal is being transmitted to wireless stimulator device 114), the RF switch 223 is set to send the forward power signal to feedback subsystem. During the off-cycle time (when an RF signal is not being transmitted to the wireless stimulator device 114), the RF switch 223 can change to a receiving mode in which the reflected RF energy and/or RF signals from the wireless stimulator device 114 are received to be analyzed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106 during its receive cycle. For example, the telemetry signal from the wireless stimulator device 114 may be coupled to the modulated signal on the dipole antenna(s) 238, during the on and off state of the transistor circuit to enable or disable a waveform that produces the corresponding RF bursts necessary to transmit to the external (or remotely implanted) pulse generator module 106. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and sent on the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 can generate telemetry data in real time, for example, at a rate of 8 Kbits per second. All feedback data received from the implanted stimulator device 114 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244, which rectifies the signal received by the RX antenna 238. The rectified signal may be fed to the controller 242 for receiving encoded instructions from the RF pulse generator module 106. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless stimulator device 114 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the pulse generator 106. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the pulse generator 106 can reduce the RF power delivered to the body if the implanted wireless stimulator device 114 reports it is receiving excess RF power.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

Also, in some implementations, for a given stimulus pulse, the controller 250 may control the electrode interface 252 to divide the current arbitrarily (or according to instructions from pulse generator module 106) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 microseconds followed by a 400 microseconds charge-balancing phase. This stimulus cycle could be specified to repeat at a rate of 60 cycles per second. Then, for set B, the controller 250 could specify a stimulus phase with 1 mA current for duration of 500 microseconds followed by a 800 microseconds charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. The wireless stimulator device 114 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment as disclosed herein, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3A:
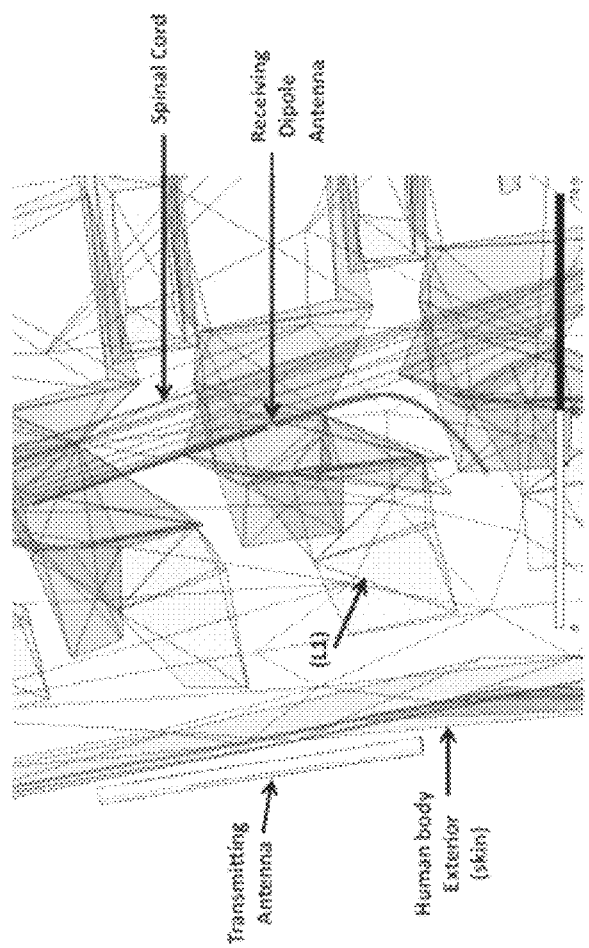
FIGS. 3A-3B illustrate an example of a transmitting antenna coupling electromagnetic energy to a receiving dipole antenna through human body tissues, according to a simulation model.
Figure 3B:
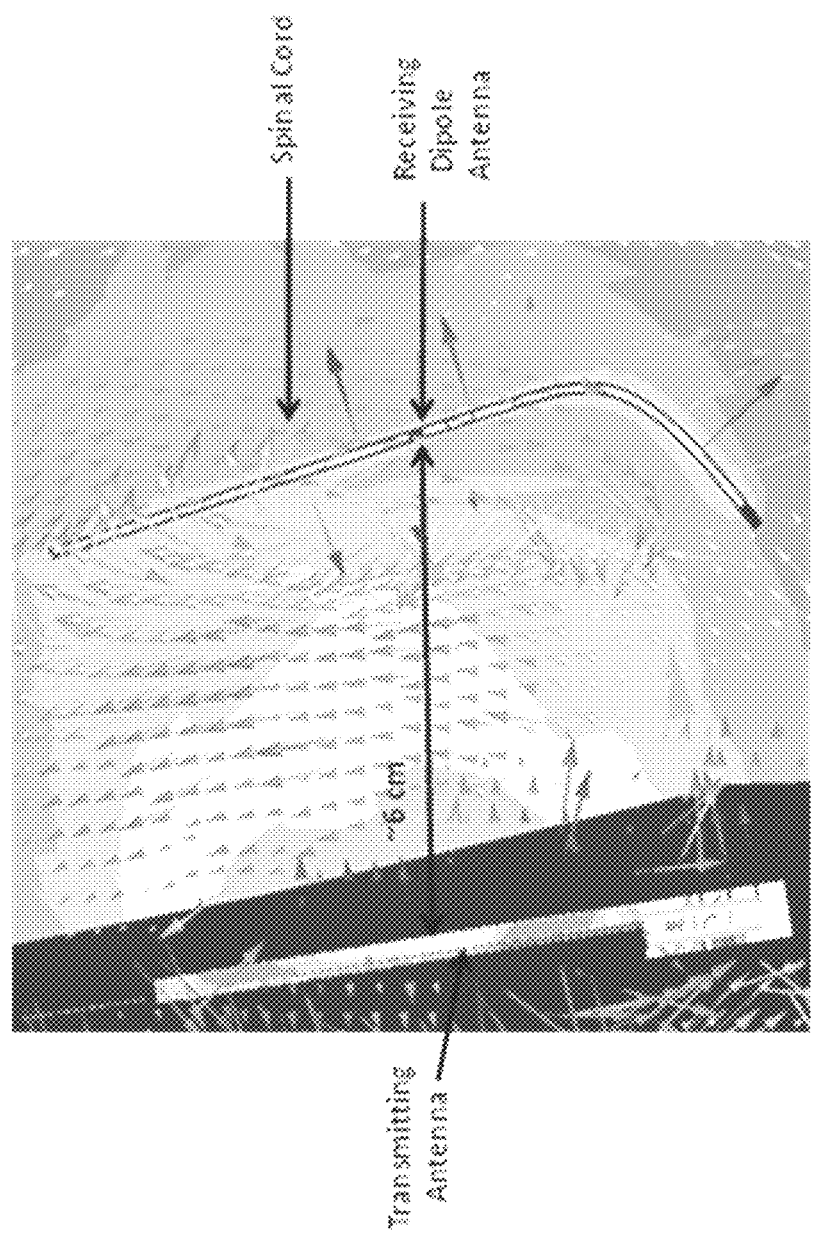

FIGS. 3A and 3B illustrate a transmitting antenna 302 coupling electromagnetic energy to a receiving dipole antenna 306 through human skin 304 and the body tissues which may include muscle, fat, tendons, and bone. In particular, FIG. 3A illustrates the transmitting antenna 1402 and its placement relative to the skin when the transmitting antenna 1402 is transmitting to the receiving dipole antenna 306 implanted in the epidural space near the spinal cord 308. In this disclosure, transmitting antenna 302 refers to the assembly of components on a device that interact with an out-bound electromagnetic wave. Such components may include dielectric layers, microstrips, signal patches, etc. In this example, the receiving dipole antenna 306 is part of an implanted stimulator device close to spinal cord 308 for stimulation thereof. Configurations may vary in the separation distance from the transmitting antenna 302 to the skin 304 as well as the depth of a receiving antenna into the human body. In some configurations, the transmitting antenna 302 may be separated from the skin 304 by a distance of as short as 2 mm. In some examples, the depth of a receiving antenna may be up to 12 cm below the skin 304. Transmitting antenna 302 can accommodate variances in separation distances when antenna 302 is appropriately configured to mitigate attenuation caused by longer distances. Such configurations may generally include tuning, matching, and polarization settings through which the average transmitting power can be increased.

In some instances, simulations may be performed to model the coupling of electromagnetic energy from the transmitting antenna prototype to a receiving dipole, for example, via radiative coupling through the electric field but not the magnetic field. In one such example, as illustrated in FIGS. 3A and 3B, the antenna is located in proximity to the spinal cord centered in the vertebrae at L1. Simulations may be run with a human body simulation model. The receiving dipole antenna 306, realistically curved, is highlighted. FIG. 3B shows the interaction of the transmitting antenna 302, the body, and the receiving dipole 306. The field of the transmitting antenna 302 is where RF energy is being coupled to the receiving antenna 306 in the body. The vector electric field is superimposed on the specific absorption rate (SAR) at the vertical cross-section containing the receiving dipole.

Figure 3C:
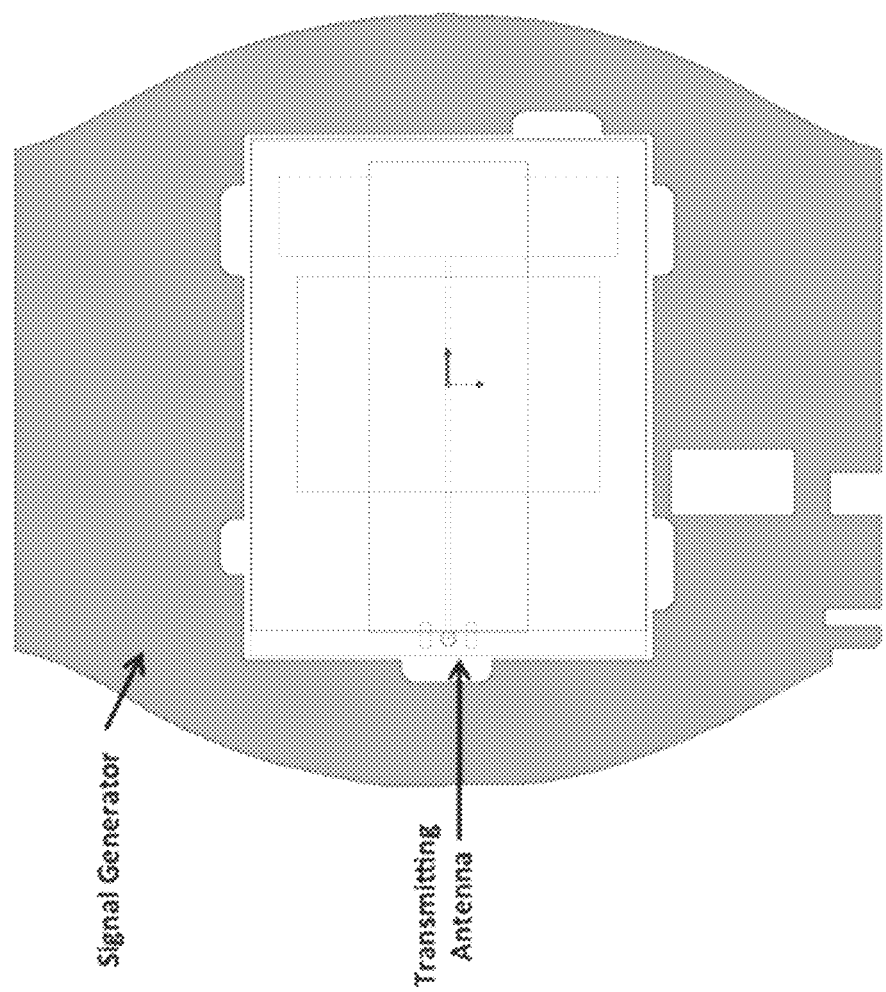
FIG. 3C is a diagram illustrating an example of placing a transmitting antenna relative to a signal generator circuit board.

FIG. 3C is a diagram illustrating the placement of transmitting antenna 202 relative to signal generator 310. Also, signal generator 310 can include a programmable device, such as a programmable module 102 in FIGS. 1 and 2. Signal generator 310 may surround the transmit antenna 302. In some instances, signal generator 310 can be placed behind or in front of transmit antenna 302. In other instances, signal generator 310 and transmitting antenna 302 may form an integral package to couple electromagnetic energy to the implanted receiving antenna 306. Signal generator 310 and transmitting antenna 302 may be worn by a subject such that a surface of the transmitting antenna 302 faces the subject's skin.

In various implementations, the antenna footprint may be smaller than the electromagnetic (EM) free space wavelength. For example, at 300 MHz, the free space wavelength of the EM wave is approximately 1 m. In this example, the footprint of the patch antenna assembly can be no more than 40 cm in diameter or length. In many instances, the maximum dimension of the antenna to free space electromagnetic wavelength ratio is on the order of 0.4. That is, the free space EM wavelength is about 2.5 times the maximum dimension of the patch antenna on a patch antenna assembly. Thus, these patch antennas are referred to as sub-wavelength antennas. Such arrangement may result from space limitations on a transmitting antenna assembly for comfort, function, and visual appeal. For the transmitting antenna assembly to transmit energy into the body and wirelessly power the embedded implants through radiative coupling, the transmitting antenna is generally associated with a small footprint laterally and a small profile in the depth dimension. Example dimensions will be demonstrated below in association with FIGS. 4A-4B. The combination for both a small profile and small footprint may also improve the overall ergonomics for the patient when using the medical device.

For example, the dimension may improve the comfort level of the patient while helping the patient to conceal the medical device from plain sight.

FIGS. 4A-4B show an example transmitting antenna 302 configured as a patch antenna assembly 400. In this disclosure, transmitting antenna 302 includes various components on an antenna device which interact with out-bound electromagnetic waves. Such components may include dielectric layers, ground planes, microstrips, signal patches, etc. FIG. 4A depicts a front view of the patch antenna assembly 400 including a signal metal layer 402, ground plane 404, and dielectric layer 406. As illustrated in the example a patch antenna assembly 400 may range from 30 mm to 150 mm in length, from 20 mm to 130 mm in width, and from 2 mm to 5 mm in thickness. The back view, as depicted in FIG. 4B, shows signal metal layer 402, ground plane 404, which can be a flexible material, dielectric 406, capacitance adjustment pad 408, microstrip 410, and ground connection 412. Each of these subcomponents may be adapted for improved performance of patch antenna assembly 400. In this illustration, signal metal layer 402 is the top most layer. When the patch antenna assembly 400 is placed close to a human body, the signal metal layer 402 is the layer of the assembly closest to the human body tissue. The patch antenna assembly 400 radiates EM radiative energy into the human body through the dielectric layers, ground planes, microstrips, signal patches, etc. The signal metal layer 402 may also be known as the radiation patch, or the signal patch.

In some instances, electromagnetic waves may be directed to flow from signal metal layer 402 into the human body and propagate at a greater depth than untuned antennas (or ones without the adjustment pad 408). Untuned antennas may have twice the surface area as the example patch antenna assembly 400. By tuning patch antenna assembly 400, the exact resonant frequency can be adjusted for more efficient transmission into tissue and improved reception by the receiving antenna. For example, when the transmitting antenna is tuned to the resonant frequency of the receiving antenna, energy transmission can be more efficient. In other words, tuning can improve transmission efficiency.

Signal metal layer 402 communicates with microstrip 410 via electromagnetic coupling. In the example shown in FIGS. 4A and 4B, this electromagnetic coupling is through slot 414 in ground plane 404. Here, the slotted ground plane is shaped to form a slot. The size and dimension of the slot generally determines a resonant frequency of the patch antenna assembly 400. As illustrated, microstrip 410 is a rod-like structure, which has a longitudinal direction (or axial direction). Microstrip 410 induces the electromagnetic (EM) waves to be linearly polarized along the longitudinal direction of microstrip 410. The end of microstrip 410 is attached to the capacitance adjustment pad 408. Capacitance adjustment pad 408 provides a capacitance for fine-tuning a resonant frequency of the patch antenna assembly 400. The capacitance adjustment pad 408 may adjust the resonant frequency on the magnitude of KHzs and may be used to adjust the resonant frequency of the patch antenna assembly to substantially match the resonant frequency of the receiving antenna. In some instances, the size (such as the length and width) of capacitance adjustment pad 408 can be set for fine tuning the resonant frequency of patch antenna assembly 400. In these instances, the length of capacitance adjustment pad 408 may be adjusted during manufacturing of the patch antenna assembly and the receiving antenna. The permittivity and thickness of the substrate of the capacitance adjustment pad 408, along with the dimensions of the capacitance adjustment pad metal, allow for a wide range of capacitance as needed for the matching of the antenna. Such capacitance adjustment affects impedance of patch antenna assembly 400. Once the thickness and dielectric is chosen for this substrate, the microstrip width is adapted for a 50Ω microstrip line impedance.

Example operating frequencies can range from around 300 MHz to 3 GHz.

FIGS. 5A-5D demonstrate further details of example configurations of a patch antenna assembly 400.

Figure 5A:
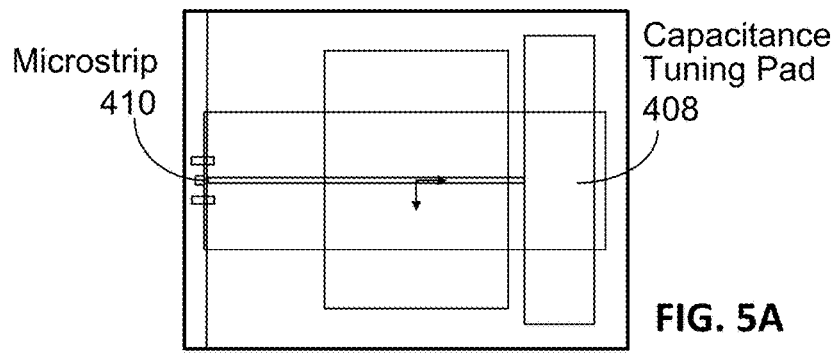
FIGS. 5A-5D demonstrate further details of the examples of configurations of a patch antenna assembly.

In particular, FIG. 5A highlights capacitance adjustment pad 408 of the patch antenna assembly 400. As illustrated, capacitance adjustment pad 408 is attached to the end of microstrip 410 to adjust the resonant frequency of the patch antenna assembly to the resonant frequency of the RF source and thereby improve transmission at the frequency of operation. This arrangement may attain a sizeable bandwidth while simultaneously maintaining a small antenna footprint. In some examples, the bandwidth of the pass band (defined as the 3 dB bandwidth) may be 100 MHz or more with a quality factor (Q) no more than 9.

Figure 5B:
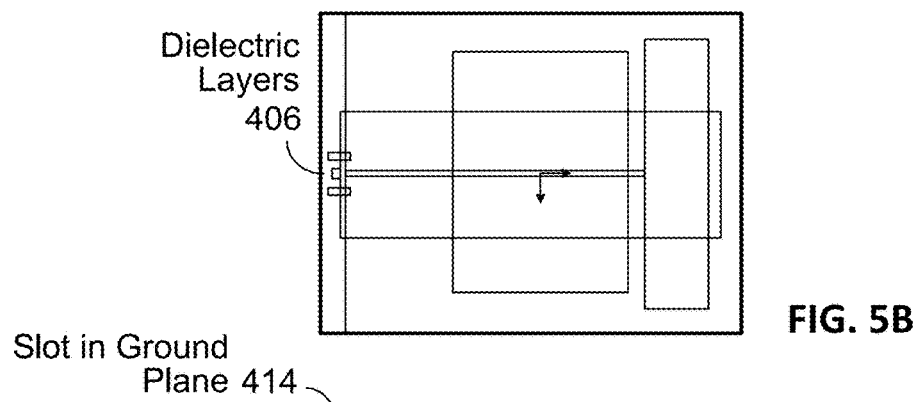
Figure 5C:
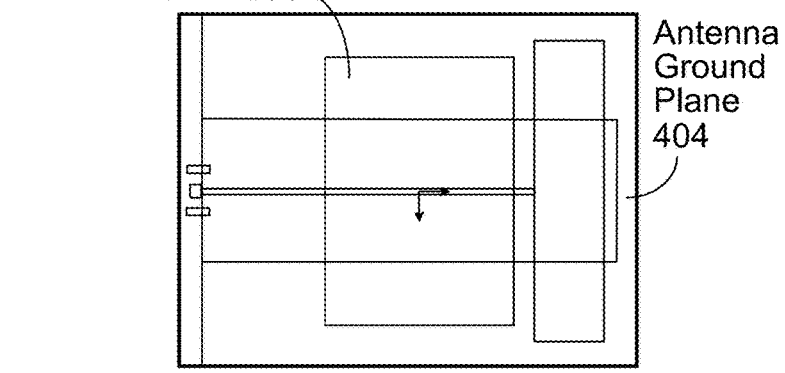
Figure 5D:
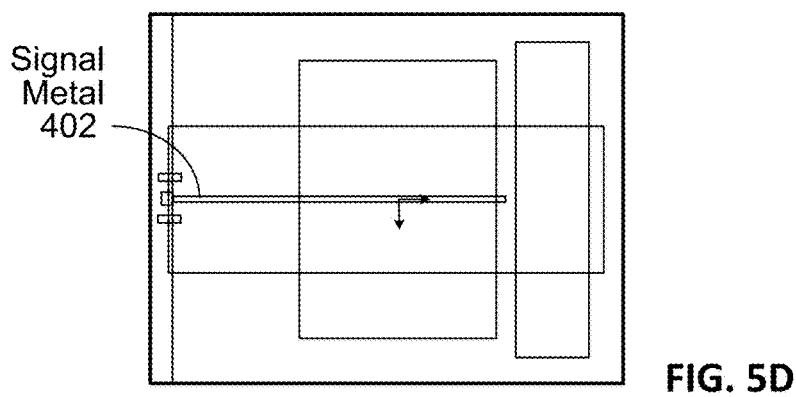

FIG. 5B highlights the dielectric layers 406 on patch antenna assembly 400. As illustrated, the type of the dielectric layer may correspond to a specific permittivity of the substrate layer. When the permittivity and the thickness of the substrate layer are determined, the microstrip size (such as a width or length) is optimized for a 50Ω microstrip line impedance. Here, the permittivity and thickness of the dielectric layer 406 that separates the signal metal layer 402 from the ground plane 414 can be designed for optimum coupling from the microstrip to the antenna signal metal layer. For illustration, FIG. 5C shows antenna assembly 400 with ground plane 414 highlighted while FIG. 5D shows antenna assembly 400 with signal metal layer 402 highlighted.

FIG. 6 shows an example of a layered configuration for patch antenna assembly 400 through a profile view. The signal metal dimensions are used as the variables for tuning the resonant frequency for optimum energy transfer to the receiving antenna 306 embedded in body tissue. Here, optimum energy transfer refers to the distribution and directivity of electromagnetic (EM) wave propagation. In one aspect, the EM radiation pattern as well as the resonant frequency of patch antenna assembly 400 matches those of receiving antenna 306. In another aspect, the polarization of EM waves emitted from patch antenna assembly 400 is aligned with the direction of the polarization of the receiving antenna. By varying the dimensions of the patch antenna assembly 400, patch antenna assembly 400 can be tuned to be in general agreement with free space transmission to a receiving antenna. Here, the dimensions of the signal metal layer 402 is adjusted to match the impedance at the face of the transmit antenna to the impedance of the body at the desired transmission frequency. For an antenna that includes stacked layers as illustrated in FIG. 6, the thickness of the dielectric layers in signal metal layer substrate 602 and microstrip and capacitance adjustment pad metal layer substrate 606 may be configured to maintain usability of the antenna for medical devices. Here, usability refers to the possibility of device displacement during use. For example, small size means ergonomically comfortable and less likely to be displaced during use. Hence, small form factor or thin thickness can be more user-friendly. In some configurations, signal metal layer substrate 602 is 2 mm in thickness. In some instances, microstrip and capacitance adjustment pad metal layer substrate 606 is 0.6 mm in thickness. Likewise, the thickness of ground plane metal layer 604 and microstrip and capacitance adjustment pad metal layer 608 may be adjusted. In some instances, the metal thickness of capacitance adjustment pad metal layer 608 is 70 μm. Moreover dielectric layers 406 may be of sufficient thickness to provide a separating layer between microstrip 410 and signal metal layer 402, leading to, for example, a 50Ω impedance.

Figure 7A:
FIG. 7A-7B show examples of radiation patterns of a patch antenna assembly.
Figure 7B:
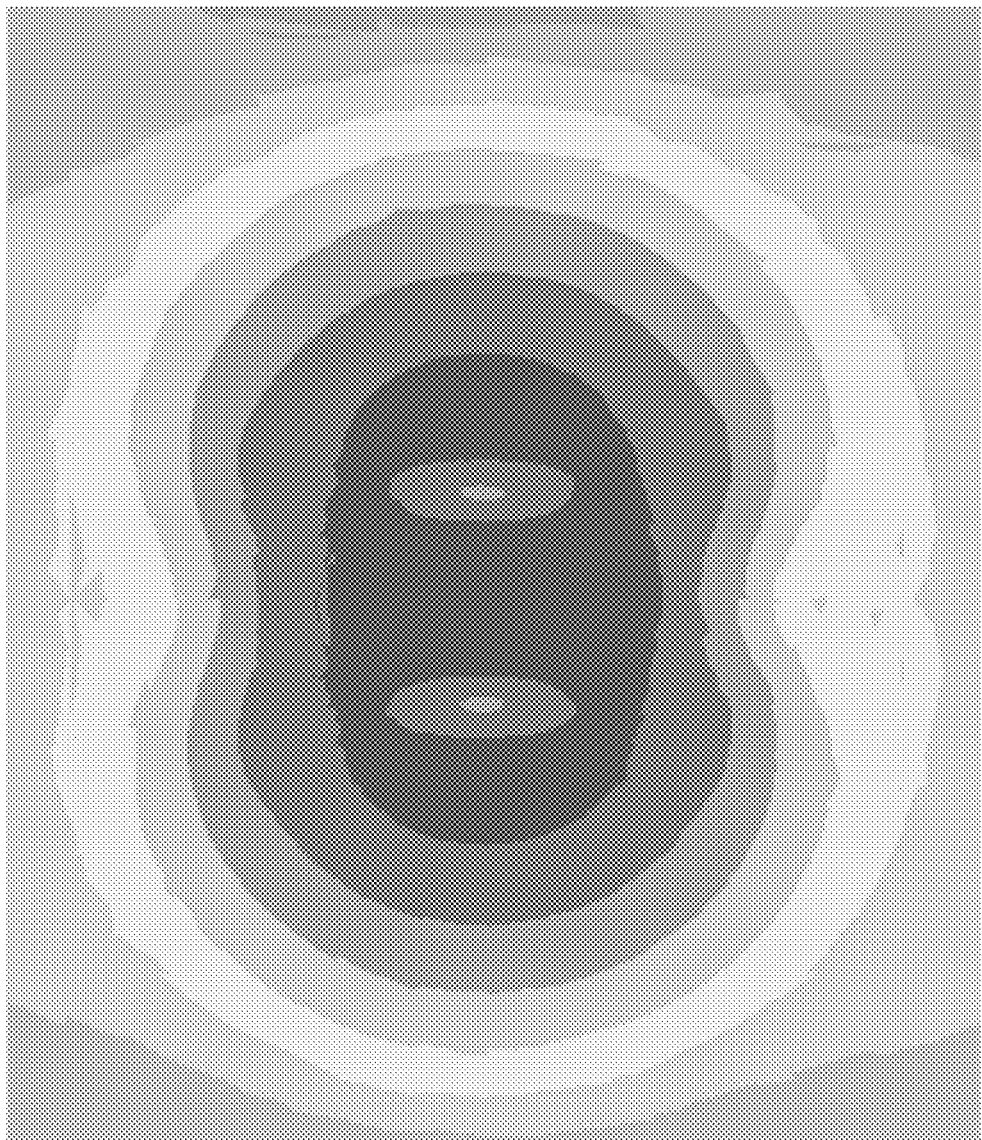

FIG. 7A-7B show examples of radiation patterns from a patch antenna assembly. FIG. 7A illustrates the planar radiation pattern from a profile view in the depth direction. The antenna radiates energy directly into the body where the radiation behind the antenna is minimal. Such transmission pattern with reduced backward propagation is a benefit of the patch design and can effectively mitigate backward radiated emissions from impacting devices other than the implanted stimulator device.

FIG. 7B illustrates an axial view of an example of the radiation pattern from the antenna. This example of the radiation pattern is an axial view taken various distances from the skin's surface and when the electromagnetic energy has been emitted from the antenna assembly and through a piece of urethane (for use as a casing material). In one example, the antenna assembly is encased in a waterproof case that is comfortable for a patient to wear. A rubber like material such as a urethane may be used to house wearable electronics. The antenna has been designed to radiate into the body through the urethane housing. The radiation pattern may be simulated with varying parameters for the antenna assembly. For example, the average input power may be varied from 50 mW to 200 mW. In another simulation setting, the distance from the skin surface may be varied from 1 mm to 2 mm.

When the receiving antenna 306 is a dipole antenna, the electric field that is not co-polarized with the dipole may not be received by the receiving antenna. The polarizations of electric field contribute to SAR levels in the body. Meanwhile, the electric field component that is perpendicular to the receiving dipole may not be received. Thus, these field components may produce additional specific absorption rate (SAR), without adding transmission benefit. To effectively leverage the SAR such that transmitted electromagnetic energy is preferentially utilized at the receiving dipole antenna, the transmit antenna can be linearly polarized. By judicious configurations, the geometry and dimensions of the signal metal 402 and ground plane 404 can cause the near field of the transmit antenna 1402 to be linearly polarized. In one configuration, the direction of microstrip 410 determines the directivity of the EM radiation, as discussed above in association with FIG. 4B and FIG. 5A.

Figure 8A:
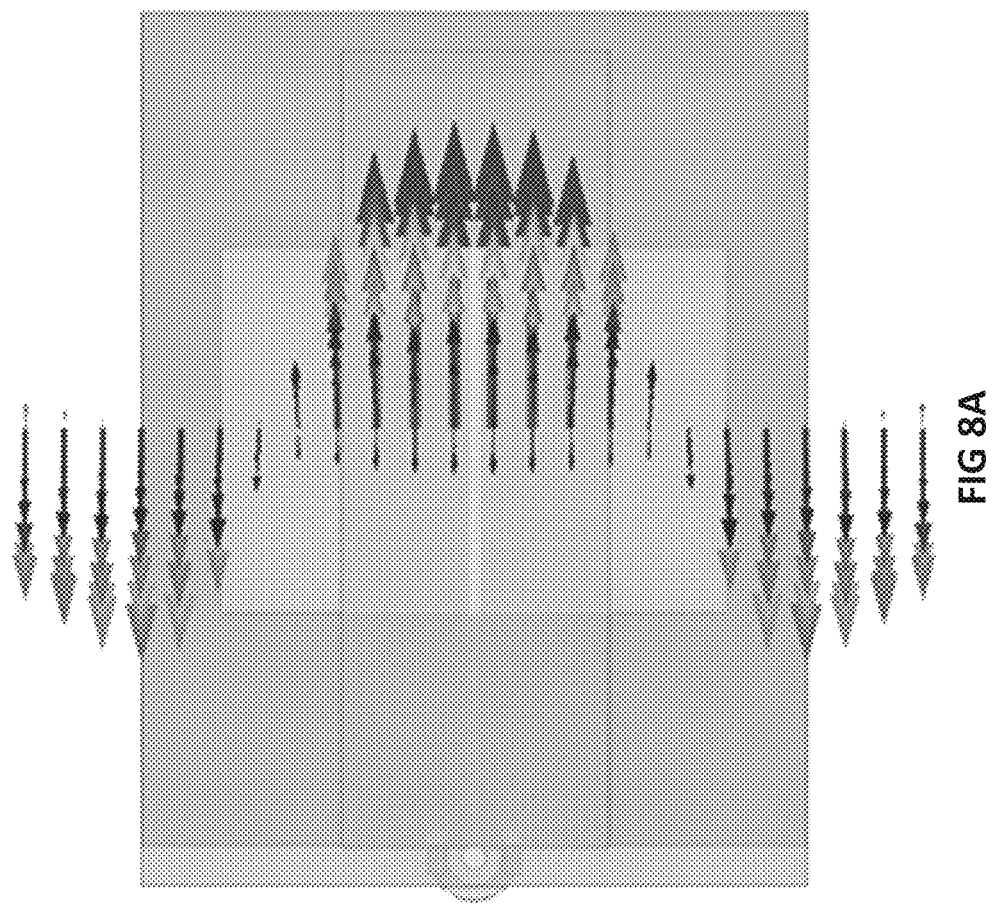

FIG. 8A-8B show example polarization patterns of electromagnetic radiation from a patch antenna assembly. In particular, FIGS. 8A and 8B show the electric field polarization for a simulation of the antenna transmitting into a human body phantom in front of the transmitting antenna 302. In comparison, FIG. 8A shows the vector field of the EM radiation from transmitting antenna 302 on the plane of the transmitting antenna 302 while FIG. 8B shows the vector field of the EM radiation from the transmitting antenna 802 on a plane that is perpendicular to the transmitting antenna 802.

Figure 9:
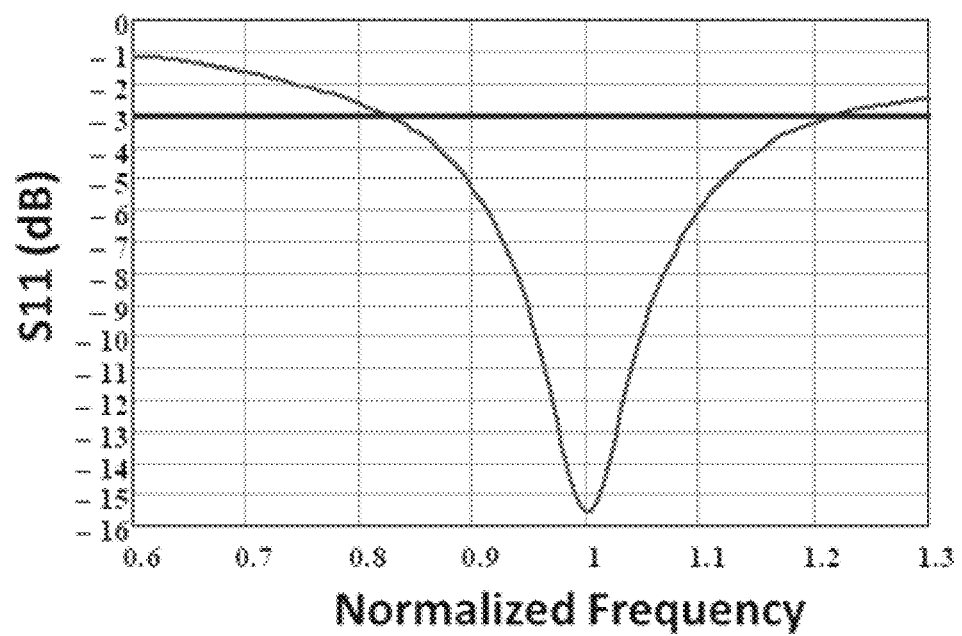
FIG. 9 shows an example of an impedance profile for a patch antenna assembly.

FIG. 9 shows an example impedance profile for the patch antenna assembly 400. Here the measured impedance is from a prototype placed on a body phantom. The measured impedance profile is plotted against a normalized frequency. The absolute resonant frequency of this prototype is not shown because the general design frequency range varies, depending on the application. Nonetheless, the quality factor of this prototype using the 3 dB bandwidth is 2.6, much lower than the maximum allowed (quality factor of 9), attesting to the broadband operation. Further, as shown in FIG. 9, the S11 parameter is under −10 dB and, more specifically, is approximately −15.5 dB. Accordingly, the patch antenna assembly is configured to have a reflection ratio of at least 10 dB at the operating frequency. The reflection ratio corresponds to a ratio of the transmission power used by the patch antenna assembly to emit the linearly polarized electromagnetic energy and the reflection power seen by the patch antenna assembly resulting from electromagnetic emission using the transmission power. The transmission power represents the power level used by the transmitting antenna—patch antenna assembly 400—in emitting linearly polarized electromagnetic energy so that the input signal containing electrical energy is sent to the receiving dipole antenna on the implantable stimulator device. Meanwhile, the reflection power refers to the reflected power back to the RF source generator—patch antenna assembly 400. A 15 dB or more reflection means about 3% of the transmitted energy may get reflected. In other words, about 97% of the transmitted energy passes through. The reflection ration of at least 10 dB may be maintained regardless of a separation between the patch antenna assembly 400 and the patient's skin (and particularly with an air gap there between) and without a coupling gel between the patch antenna assembly 400 and the patient's skin. The patch antenna assembly 400 may be configured such that the reflection ratio at the operating frequency of the antenna assembly is maintained when the antenna assembly is positioned between zero to 2 centimeters, or more particularly, between zero to 1 centimeter, away from the patient's skin. That is, the antenna assembly 400 may be configured such that the S11 parameter notch at the operating frequency is wide enough that the S11 parameter remains below −10 dB as the antenna assembly 400 is positioned between 0 to 2 centimeters, or more particularly, between zero to 1 centimeter, away from the patient's skin.

A number of implementations have been described. Nevertheless, it will be understood that various modifications may be made. Accordingly, other implementations are within the scope of the following claims.

What is claimed is:

1. A patch antenna assembly, comprising:
    a signal metal layer configured to emit linearly polarized electromagnetic energy to a receiving antenna implanted up to 12 cm underneath a subject's skin, and oriented to face the subject's skin when the patch antenna assembly is worn by the subject;
    a signal metal layer substrate on which the signal metal layer is positioned;
    a ground plane located next to the signal metal layer substrate and further away from the subject's skin than the signal metal layer when the patch antenna assembly is worn;
    a microstrip and capacitance adjustment pad metal layer substrate located next to the ground plane and away from the signal metal layer; and
    a microstrip and capacitance adjustment pad metal layer next to the microstrip and capacitance adjustment pad metal layer substrate and away from the signal metal layer, the microstrip and capacitance adjustment pad metal layer comprising:
    a capacitance adjustment pad configured to adjust a resonant frequency of the patch antenna assembly; and
    a microstrip attached to the capacitance adjustment pad and configured to induce the emitted electromagnetic energy to be linearly polarized along a longitudinal direction of the microstrip.

2. The patch antenna assembly of claim 1, wherein the patch antenna assembly is configured to operate with a reflection ratio of at least 10 dB, the reflection ratio corresponding to a ratio of a transmission power used by the patch antenna assembly to emit the linearly polarized electromagnetic energy and a reflection power seen by the patch antenna assembly resulting from electromagnetic emission using the transmission power.

3. The patch antenna assembly of claim 1, wherein the reflection ratio of at least 10 dB is maintained regardless of a separation between the signal metal layer and the subject's skin.

4. The patch antenna assembly of claim 1, wherein the patch antenna assembly is configured such that the reflection ratio of at least 10 dB is maintained with an air gap and without gel coupling between the signal metal layer and the subject's skin.

5. The patch antenna assembly of claim 1, wherein the capacitance adjustment pad is configured to adjust the resonant frequency of the patch antenna assembly to be matched at the resonant frequency of a RF signal generator.

6. The patch antenna assembly of claim 1, wherein the patch antenna assembly is configured to operate with a quality factor (Q) no more than 9.

7. The patch antenna assembly of claim 1, wherein the patch antenna assembly has a size that is no more than 40% of a wavelength of the emitted electromagnetic energy.

8. The patch antenna assembly of claim 7, wherein the patch antenna assembly has a length between 30 and 150 mm, a width between 20 and 130 mm, and a thickness between 2 and 5 mm.

9. The patch antenna assembly of claim 8, wherein the signal metal layer substrate is about 2 mm thick, the microstrip and capacitance adjustment pad metal layer substrate is about 0.6 mm thick, and the capacitance adjustment pad metal layer is about 70 μm thick.

10. The patch antenna assembly of claim 1, wherein the patch antenna assembly is configured to operate at a particular frequency between 800 MHz and 5.7 GHz.

11. The patch antenna assembly of claim 1, wherein the ground plane comprises a slot sized and shaped to determine a resonant frequency of the patch antenna assembly.

12. The patch antenna assembly of claim 1, wherein the capacitance adjustment pad is configured to adjust the resonant frequency of the patch antenna assembly by an order of KHz.

13. The patch antenna assembly of claim 1, further comprising:
    a dielectric layer between the signal metal layer and the ground plane, the dielectric layer constructed to improve a coupling of the emitted linearly polarized electromagnetic energy from the microstrip to the signal metal layer relative to when the dielectric layer is absent.

14. The patch antenna assembly of claim 12, wherein the microstrip is sized and shaped for a 50Ω line impedance in the presence of the dielectric layer.

15. A system, comprising:
    a Radio Frequency (RF) signal generator configured to be worn by a subject and programmed to generate an input signal containing electrical energy and stimulation pulse parameters, and
    a patch antenna assembly coupled to the signal generator and configured to receive the input signal from the signal generator and then transmit the input signal to a receiving dipole antenna of a passive stimulator device implanted up to 12 cm underneath the subject's skin such that the patch antenna assembly operates with a reflection ratio of at least 10 dB, the reflection ratio corresponding to a ratio of a transmission power used by the patch antenna assembly to transmit the input signal and a reflection power seen by the patch antenna assembly resulting from electromagnetic emission using the transmission power, the patch antenna assembly comprising:

a signal metal layer configured to transmit the input signal using linearly polarized electromagnetic energy to the receiving dipole antenna, and oriented to face the subject's skin when the patch antenna assembly is worn by the subject;

a signal metal layer substrate on which the signal metal layer is positioned;

a ground plane located next to the signal metal layer substrate and further away from the subject's skin than the signal metal layer when the patch antenna assembly is worn;

a microstrip and capacitance adjustment pad metal layer substrate located next to the ground plane and away from the signal metal layer; and a microstrip and capacitance adjustment pad metal layer next to the microstrip and capacitance adjustment pad metal layer substrate and away from the signal metal layer, the microstrip and capacitance adjustment pad metal layer comprising:

a capacitance adjustment pad configured to adjust a resonant frequency of the patch antenna assembly; and a microstrip attached to the capacitance adjustment pad and configured to induce the emitted electromagnetic energy to be linearly polarized along a longitudinal direction of the microstrip; and a passive neural stimulator device configured to be implanted underneath the subject's skin, the passive neural stimulator device comprising:

a receiving dipole antenna configured to receive the input signal emitted from the antenna assembly; and circuitry coupled to the receiving dipole antenna, the circuitry being configured to:

extract electric energy contained in the input signal; and use the extracted electrical energy to create stimulation pulses suitable for stimulating neural tissue, the stimulation pulses being created according to the stimulation pulse parameters.

16. The system of claim 15, wherein the capacitance adjustment pad is configured to adjust the resonant frequency of the patch antenna assembly to match the resonant frequency of the RF signal generator.

17. The system of claim 16, wherein the capacitance adjustment pad is configured to adjust the patch antenna assembly by an order of KHz.

18. The system of claim 15, wherein the patch antenna assembly is configured to operate with a quality factor (Q) no more than 9.

19. The system of claim 15, further comprising:

a dielectric layer that separates the signal metal layer from the ground plane, the dielectric layer constructed to improve a coupling of the emitted linearly polarized electromagnetic energy from the microstrip to the signal metal layer relative to when the dielectric layer is absent.

20. The system of claim 19, wherein the microstrip is sized and shaped for a 50Ω line impedance in the presence of the dielectric layer.

* * * * *